United States Patent [19]

Haruta et al.

[11] Patent Number: 5,051,394

[45] Date of Patent: Sep. 24, 1991

[54] METHOD FOR PRODUCTION OF ULTRA-FINE GOLD PARTICLE-IMMOBILIZED OXIDES

[75] Inventors: Masatake Haruta; Tetsuhiko Kobayashi; Susumu Tsubota; Yoshiko Nakahara, all of Ikeda, Japan

[73] Assignees: Agency of Industrial Science & Technology; Ministry of International Trade & Industry, both of Tokyo, Japan

[21] Appl. No.: 484,238

[22] Filed: Feb. 26, 1990

[30] Foreign Application Priority Data

Mar. 24, 1989 [JP] Japan .................................. 1-73603

[51] Int. Cl.$^5$ .............................................. B01J 23/52
[52] U.S. Cl. .................................. 502/324; 502/330; 502/343; 502/344; 502/345
[58] Field of Search ............... 502/324, 330, 343, 344, 502/345

[56] References Cited

U.S. PATENT DOCUMENTS 4,698,324 10/1987 Haruta et al. ................... 502/344 X
4,839,327 6/1989 Haruta et al. ................... 502/344 X
4,937,219 6/1990 Haruta et al. ....................... 502/174

FOREIGN PATENT DOCUMENTS 60-238148 11/1985 Japan .
62-155937 7/1987 Japan .
63-252908 10/1988 Japan .

OTHER PUBLICATIONS

Chemistry Express, vol. 3, No. 3, pp. 159–162, 1988, M. Haruta et al., "Preparation and Catalytic Properties of Gold Finely Dispersed on Beryllium Oxide".
Journal of Catalysis, vol. 115, pp. 301–309, 1989, M. Haruta et al., "Gold Catalysts Prepared by Coprecipitation for Low-Temperature Oxidation of Hydrogen and of Carbon Monoxide".
Successful Design of Catalysts, 1988, pp. 33–42, M. Haruta et al., "Fine Structure of Novel Gold Catalysts Prepared by Coprecipitation".
Government Industrial Research Institute of Osaka, AIST, MITI, Jul. 6, 1987, pp. 407–414, M. Haruta, "Ultrafine Gold Particles Immobilized by Coprecipitation with Metal Oxides–Their Fine Structures and Applications to Combustion Catalysts"...
Chemistry Letters, pp. 405–408, 1987, M. Haruta et al., "Novel Gold Catalysts for the Oxidation of Carbon Monoxide at a Temperature Far Below 0° C.".

Primary Examiner—W. J. Shine
Attorney, Agent, or Firm—Oblon, Spivak, McClelland, Maier & Neustadt

[57] ABSTRACT

An ultra-fine gold particle-immobilized oxide is produced by a method which comprises adding an alkali compound to an aqueous solution containing a gold compound and a water-soluble metal salt thereby giving rise to a coprecipitate in the aqueous solution, separating the coprecipitate from the aqueous solution, and calcining the separated coprecipitate. This method is characterized by allowing the presence of a carboxylic acid or a carboxylate in the aqueous solution from the beginning or after the occurrence of the coprecipitate.

20 Claims, 6 Drawing Sheets

MOLAR RATIO OF CALCIUM OXALATE ADDED TO $HAuCl_4$

METHOD FOR PRODUCTION OF ULTRA-FINE GOLD PARTICLE-IMMOBILIZED OXIDES

BACKGROUND OF THE INVENTION

1. Field of the Invention

This invention relates to methods for the production of ultra-fine gold particle-immobilized oxides.

Gold has been considered to be typical of metals which are low in chemical activity. It has been reported by some of the present inventors that when gold is dispersed and deposited as ultra-fine particles smaller than 10 nm in diameter on the oxide of such a metal as iron, cobalt, or nickel, the gold becomes a highly active catalyst. ["Chemistry Express", 3, 159–162 (1988), and J. Catalysis", 115, 301–309 (1989)].

2. Prior Art Statement

The following five methods have been developed by some of the present inventors for the production of such an ultra-fine gold particle-immobilized metal oxides as described above.

1) Coprecipitation method (Japanese Patent Public Disclosure SHO 60(1985)-238,148)

A composite having an ultra-fine gold particle immobilized on the oxide of such a metal as iron, cobalt, nickel, or copper is obtained by preparing a mixed aqueous solution having dissolved therein such a water-soluble salt as iron, cobalt, nickel, or copper and a water-soluble compound of gold, neutralizing the mixed aqueous solution with an aqueous alkali solution thereby giving rise to a coprecipitate, washing the coprecipitate with water, and calcining the washed coprecipitate in the air.

2) Uniform deposition and precipitation method (Japanese Patent Public Disclosure SHO 62(1987)-155937)

An ultra-fine gold particle-immobilized oxide is obtained by adding urea and/or acetamide to an aqueous solution of a water-soluble gold compound, immersing a metal oxide carrier in the resultant aqueous solution, heating the aqueous solution thereby inducing hydrolysis of the urea and/or acetamide and gradual formation of ammonia and consequently allowing gold hydroxide to be deposited on the metal oxide in consequence of ensuing increase of the pH value of the aqueous solution, and washing with water and calcining in the air the resultant gold hydroxide-deposited metal oxide.

3) Dropwise neutralization and precipitation method [Japanese Patent Public Disclosure SHO 63(1988)252908]

An ultra-fine gold particle-immobilized oxide is obtained by adding dropwise an aqueous solution of a water-soluble gold compound to an aqueous solution of a metal oxide having a pH value in the range of 7 to 11 while keeping the pH value within the range mentioned above, and washing with water and calcining in the air the resultant gold hydroxide-deposited metal oxide.

4) Reductant addition method [Japanese Patent Public Disclosure SHO 63(1988)252908]

An ultra-fine gold particle-immobilized oxide is obtained by preparing a metal oxide-containing aqueous solution having a water-soluble gold compound dissolved therein and having a pH value in the range of 7 to 11, adding a reducing agent dropwise to the aqueous solution while keeping the pH value in the range mentioned above thereby inducing deposition of gold on the metal oxide, and washing with water and calcining in the air the resultant gold-deposited metal oxide.

5) pH-controlled neutralization and precipitation method [Japanese Patent Public Disclosure SHO 63(1988)-252908]

An ultra-fine gold particle-immobilized oxide is obtained by preparing a metal oxide-containing aqueous solution having a water-soluble gold compound dissolved therein and having a pH value in the range of not less than 11, blowing carbon dioxide gas therein or adding an acidic aqueous solution dropwise thereto thereby adjusting the pH value in the range of 7 to 11 and consequently inducing deposition of gold hydroxide on the metal oxide, and washing with water and calcining in the air the resultant composite metal oxide.

The five methods described above have defects of their own and are subject to restrictions regarding the amount of gold that can be immobilized in an ultra-fine form and the kind of carrier that can be used.

The coprecipitation method of 1), for example, is usable only for the production of a powdery or granular catalyst and not usable for the purpose of dispersing and depositing ultra-fine gold particles on a molded metal oxide or a shaped article having the metal oxide carried thereon. Further, this method has a problem in that the metal oxides on which gold can be effectively carried in the form of an ultra-fine particle are limited to the oxides of Cu, Fe, Co, Ni, etc.

The uniform deposition and precipitation method of 2) has a disadvantage in that accurate control of conditions of the deposition of gold hydroxide is indispensable and the work of this deposition consumes at least several hours's. This method inevitably causes partial precipitation and deposition of gold from the aqueous solution of the gold compound and, therefore, entails a disadvantage in that the utilization efficiency of gold is low and the production cost is high. Moreover, even slight variation in the conditions tends to reduce the uniformity and dispersion of the deposited gold hydroxide and to cause the gold hydroxide to be deposited in large aggregates.

The dropwise neutralization and precipitation method of 3) has a disadvantage in that when the amount of gold loading exceeds 1 wt %, the deposition and precipitation of gold hydroxide on the metal oxide tend to occur unevenly and result in aggregation of ultra-fine gold particles during the course of deposition by calcination.

The reductant addition method of 4) has a disadvantage in that when the specific surface area of the metal oxide carrier is small or when the amount of gold loading is increased, for example, the dissolved gold compound is reduced to form metal particles in solution and is not utilized effectively in the deposition of the ultra-fine gold particles on the support oxide and, consequently, the production cost rises.

The pH control neutralization and precipitation method of 5) has a disadvantage similar to that of the method of 3).

In order to improve the catalytic activities, gas sensitivities, colors of the ultra-fine gold particle-immobilized oxides so as to apply these oxides for use as a catalyst, a gas sensor, or a pigment, it becomes necessary to control the amount of gold loaded and the kind of metal oxides to be used so as to suit the purpose for which the oxides are utilized. In the preparation of ultra-fine gold particle-immobilized titanium oxide as a cosmetic material, for example, the amount of gold to be carried is desired to exceed 10% by weight for the purpose of deepening the tone of its bluish purple color. As the material for a gas sensor which operates at a low temperature and enjoys a long service life, there is required a metal oxide semiconductor having gold carried in an excess amount thereon. By the conventional methods, however, the amount of gold carried cannot be varied over a wide range. Further, these methods cannot be effectively applied to many kinds of metal oxides.

The present inventors continued a study in search of methods for the production of ultra-fine gold particle-immobilized oxides free from the disadvantages suffered by the conventional methods as described above.

SUMMARY OF THE INVENTION

As the result of this study, the inventors have found that by a method which comprises adding a carboxylic acid or a salt thereof to an aqueous solution of a gold compound and a water-soluble metal salt either during or after the formation of a coprecipitate therein due to neutralization of the aqueous solution with an alkali aqueous solution, allowing the resultant mixture to age, and then heating the coprecipitate, an oxide having ultra-fine gold particles uniformly and strongly attached thereon is obtained without allowing the ultra-fine gold particles to agglomerate and that this ultra-fine gold particle-immobilized oxide possesses extremely satisfactory properties fit not only for oxidation catalysts, reduction catalysts, and gas sensors but also for pigments. The present invention has been perfected as a result.

Specifically, this invention is directed to a method for the production of an ultra-fine gold particle-immobilized oxide, which method essentially consists of neutralizing an aqueous solution containing a gold compound and a water-soluble metal salt as essential main components thereof by addition thereto of an alkali compound thereby giving rise to a coprecipitate in the aqueous solution, then adding to the coprecipitate-containing aqueous solution at least one carboxylic acid compound selected from the group consisting of carboxylic acids and salts of the carboxylic acids, subsequently separating the coprecipitate from the aqueous solution, and heating the separated coprecipitate and to a method for the production of an ultra-fine gold particle-immobilized oxide, which method essentially consists of adding an alkali compound to an aqueous solution containing as essential main components thereof a gold compound, a water-soluble metal salt, and at least one carboxylic acid compound selected from the group consisting of carboxylic acids and salts of the carboxylic acids thereby effecting neutralization of the aqueous solution and consequent formation of a coprecipitate, separating the coprecipitate from the aqueous solution, and heating the separated coprecipitate.

The above and other features and objects of the invention will become apparent with the following detailed description made with reference to the attached drawings.

DETAILED DESCRIPTION OF THE PREFERRED EMBODIMENTS

Figure 1:
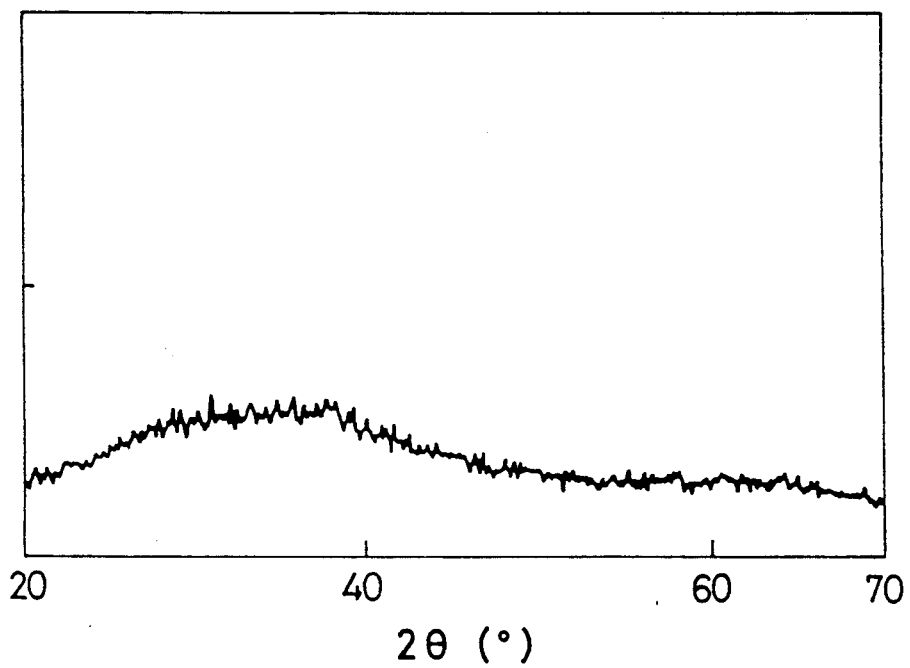
FIG. 1 is a powder X-ray diffraction diagram of an ultra-fine gold particle-immobilized oxide obtained by the method of this invention as indicated in Example 18.

In the method of this invention, an aqueous solution containing a gold compound and a water-soluble metal salt is neutralized with an alkali aqueous solution to give rise to a coprecipitate in the aqueous solution. This neutralization may be effected by any of the conventional methods such as, for example, a method which comprises adding dropwise a mixed aqueous solution containing a gold compound and a water-soluble metal salt to an alkali aqueous solution, a method which comprises adding dropwise an aqueous gold compound solution and an aqueous water-soluble metal salt solution to an alkali aqueous solution, and a method which comprises adding an alkali aqueous solution dropwise to a mixed aqueous solution containing a gold compound and a water-soluble metal salt. From the standpoint of ensuring uniformity of the particle diameter of the ultra-fine gold particles to be supported, the method which comprises adding the mixed aqueous solution dropwise to the alkali aqueous solution proves to be particularly desirable.

The gold compounds which are usable effectively herein include such water-soluble gold salts as chloroauric acid ($HAuCl_4$), sodium chloroaurate ($NaAuCl_4$), gold cyanide (AuCN), potassium gold cyanide {$K[Au(CN)_2]$}, and diethylamineauric acid trichloride [$(C_2H_5)_2NH \cdot AuCl_3$]. From the standpoint of practical use chloroauric acid is preferable. The water-soluble metal salts which are usable herein include nitrates, sulfates, chlorides, and other salts of Cu, Fe, Co, Ni, Mn, Al, Ti, Zn, Sn, Sb, etc., for example. From the standpoint of practical use, $Ti(SO_4)_2$, $TiCl_3$, $SnCl_4$, $SbCl_5$, $Zn(NO_3)_2 \cdot 6H_2O$, and $Al(NO_3)_3 \cdot 9H_2O$ are desirable.

In the aqueous solution of a gold compound and the aqueous solution of a water-soluble metal salt, it is proper for the concentration of the gold compound to fall approximately in the range of $1 \times 10^{-2}$ to $1 \times 10^{-5}$ mol/liter and the water-soluble metal salt approximately in the range of 1 to 0.01 mol/liter. In the mixed aqueous solution containing the two compounds mentioned above, the concentrations of the component compounds may fall in the respective ranges mentioned above.

The alkali aqueous solutions which are usable for the neutralization of the aqueous solution mentioned above include the aqueous solutions containing sodium carbonate, sodium hydroxide, potassium carbonate, and ammonia, for example.

In the method of this invention, a carboxylic acid or a salt thereof is allowed to exist in the aqueous solution during the course of the reaction which produces the coprecipitate mentioned above or the carboxylic acid or the salt thereof is added to the solution containing the coprecipitate after its formation.

When the carboxylic acid or the salt thereof is present during the reaction forming the coprecipitate, the amount of the alkali compound and the amount of the carboxylic acid or the salt thereof to be used are so adjusted that the aqueous solution at the end of the reaction forming the coprecipitate may fall approximately in the range of pH 5 to 12, preferably pH 6 to 8. When the carboxylic acid or the salt thereof is added after the formation of the coprecipitate, the amount of the acid or the salt is so adjusted at the time of the addition that the pH of the aqueous solution will remain in the range of 5 to 12, preferably 6 to 8. When the pH of the aqueous solution is in the range of 5 to 12 as described above, since the gold compound is incorporated as a hydroxide in the coprecipitate, virtually no reduction of the gold compound with a carboxylic acid ion occurs. It is considered that the carboxylic acid ions formed by dissociation in the aqueous solution are adsorbed on the coprecipitate, simultaneously and completely with the gold hydroxide ion $[Au(OH)_4^-]$. The carboxylic acid ions work as a kind of protective fence for separating the locations at which deposition and precipitation of the gold hydroxide occurs and thus preventing the gold hydroxide from being agglomerated.

The carboxylic acids or salts thereof (hereinafter referred to collectively as "carboxylic acid compounds") which are usable herein include glutaric acid ($HOOCCH_2CH_2CH_2COOH$), glycolic acid ($CH_2HCOOH$), oxalic acid ($HOOC.COOH$), lactic acid [$CH_3.CH(OH).COOH$], malonic acid ($HOOC.CH_2.COOH$), maleic acid ($HOOC.CH=CH.COOH$), succinic acid ($HOOC.CH_2.CH_2.COOH$), malic acid [$HOOC.CH(OH).CH_2.COOH$], tartaric acid [$HOOC.CH(OH).CH(OH).COOH$], citric acid [$HOOC.CH_2.C(OH)(COOH).CH_2COOH$], and potassium, sodium, magnesium, strontium, barium, manganese, cobalt, nickel salts of such acids, for example.

Among these carboxylic acid compounds enumerated above, citric acid, maleic acid, magnesium citrate, trisodium citrate, potassium tartrate, barium succinate, manganese oxalate, calcium oxalate, cobalt malonate, nickel glutarate, strontium malate, calcium glycolate, barium tartrate, and cobalt citrate are preferable.

The amount of the carboxylic acid compound to be added is generally required to be at least 1 mol per mol of the gold to be supported, though it is variable with the kind of compound to be used and the method of addition to be employed. When the carboxylic acid compound is not readily dissociable, this amount may be increased up to about 30 mols. In the case of a carboxylate such as, for example, trisodium citrate which is readily dissociable, the amount of its addition is decreased to the smallest allowable extent in which the pH of the aqueous solution is not appreciably varied by the addition of $Na^+$ ion.

The presence of the carboxylic acid compound during the formation of the coprecipitate can be attained by a method which comprises adding the aqueous solution of a carboxylic acid compound dropwise during the course of mixture of the aqueous solution containing a gold compound and a water-soluble metal salt with an alkali aqueous solution or a method which comprises having a carboxylic acid compound added in advance to the alkali aqueous solution.

When a carboxylic acid compound is added after the formation of the coprecipitate, the aqueous solution of the carboxylic acid compound is desired to be added within about one hour, preferably 30 minutes, following the formation of the coprecipitate.

The method for the addition of the carboxylic acid compound and the amount of addition thereof may be determined in due consideration of the pH of the aqueous solution and the dissociation equilibrium of the carboxylic acid compound. They are desired to be such that the carboxylic acid ion generated by dissociation in the aqueous solution containing the coprecipitate will show a concentration in the range of 0.0001 to 0.01 mol/liter. If the concentration of the carboxylic acid ion exceeds 0.01 mol/liter, the carboxylic acid ion is adsorbed on the substantially entire surface of the coprecipitate and the gold complex ion remaining in the liquid phase is inhibited from being adsorbed. Further, since the carboxylic acid ion reduces the gold complex ion and gives rise to colloidal gold particles in the liquid phase, there arises a problem that the amount of gold to be effectively supported on the coprecipitate decreases. Conversely, if the concentration of the carboxylic acid ion is less than 0.0001 mol/liter, the amount of the carboxylic acid ion to be adsorbed on the coprecipitate is too small for the effect of preventing the agglomeration of the gold hydroxide to be manifested sufficiently. When sodium citrate which is readily dissociable is used as a carboxylate, for example, the concentration of the citric acid ion in the liquid phase exceeds 0.01 mol/liter temporarily if the salt is added in a large amount all at once. The addition of this salt, therefore, is desired to be made gradually. In the case of magnesium citrate, it can be handled very easily because this salt is not easily dissociable and, consequently, is dissociated only partly into citric acid ion even if it is added in its whole amount all at once. At pH=9.6, for example, since the ratio of the citric acid ion to magnesium citrate is 1:17, only 1/18 of the added magnesium citrate is dissociated into citric acid ion. When the citric acid ion is adsorbed on the coprecipitate from the liquid phase, the liquid phase is replenished with citric acid ion newly formed by the dissociation. Thus, it suffices to adjust the amount of the magnesium citrate to be added in consideration of the dissociation equilibrium and the pH so that the concentration of the citric acid ion in the liquid phase will remain in the range of 0.01 to 0.0001 mol/liter at all times.

In the method of this invention, after the procedure described above is completed, the solution of the coprecipitate is desired to be aged by stirring for not less than 30 minutes. At the end of the aging, the pH of the solution is desired to be approximately in the range of 5 to 12, preferably 6 to 8.

In the present invention, the operation for the formation of the coprecipitate and the operation for the addition of the carboxylic acid compound are desired to be carried out at a solution temperature approximately in the range of 20° C. to 90° C.

The amount of the gold compound to be used is determined by the amount of the ultra-fine gold particle to be immobilized on the metal oxide. The upper limit of this amount, though variable with the kind, form, specific surface area, etc. of the metal oxide to be used, generally falls approximately in the range of 0.5 to 10% (1 to 40% by weight) in atomic % of gold in the total amount of metals.

When the coprecipitated hydroxide of gold and carrier metal obtained by the method described above is superheated, the hydroxide of gold in the coprecipitate is decomposed into gold and this gold is uniformly immobilized strongly attached in the form of ultra-fine particles on the metal oxide. The heating temperature is desired to be approximately in the range of 100° C. to 800° C. and the heating time to be approximately in the range of 1 to 24 hours.

In the ultra-fine gold particle-immobilized oxide which is obtained by the method of this invention, the ultra-fine gold particles are of small diameter and a narrow range of diameter distribution and are uniformly immobilized. The diameter of the ultra-fine gold particles is generally in the range of 3 to 10 nm.

Figure 2:
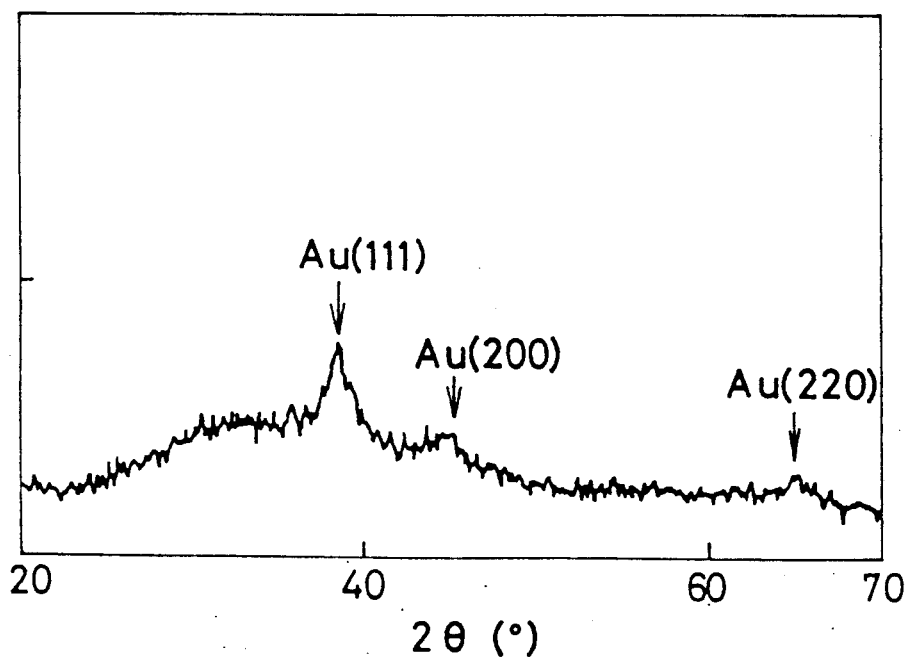
FIG. 2 is a powder X-ray diffraction diagram of an ultra-fine gold particle-immobilized oxide obtained without the addition of a carboxylate as indicated in Example 18.

FIG. 1 and FIG. 2 shows the results of the experiment of Example 18 to be described specifically hereinafter. To be specific, FIG. 1 is a powder X-ray diffraction diagram of an ultra-fine gold particle-immobilized oxide ($Au/TiO_2$) obtained by the method of this invention, using magnesium citrate as a carboxylate and FIG. 2 is a powder X-ray diffraction diagram of an ultra-fine gold particle-immobilized oxide ($Au/TiO_2$) obtained by the same method, except that the addition of a carboxylate was omitted. Comparison of the data of FIG. 1 and those of FIG. 2 reveals that immobilization of ultra-fine gold particles can be obtained by the method of this invention.

The metal oxide having gold immobilized thereon in a finely dispersed state by the method of this invention can be used in various products such as, for example, oxidation catalysts, reduction catalysts, gas sensors, and pigments.

Since the ultra-fine gold particle-immobilized oxide of this invention can catalyze the combustion of such fuels as hydrogen, carbon monoxide, methanol, and propane in wide ranges of concentration at relatively low temperatures not exceeding 300° C., it can be used advantageously as an oxidation catalyst in various space heaters and kitchen heaters with catalytic combustion systems. It can also be used as a catalyst for cleaning waste gases emitted from kerosene stoves, oil fan heaters, and gas fan heaters and as a catalytic filter in air conditioners for cleaning the air. It is also useful as a catalyst for oxidizing treatment of solvents in coating industry and as a catalyst for cleaning effluent gases from plants.

When the ultra-fine gold particle-immobilized oxide is used as an oxidation catalyst, it is desired to contain gold in a concentration approximately in the range of 0.5 to 10 atomic %. Particularly when the ultra-fine gold particle-immobilized oxide is used for the oxidation of carbon monoxide at a temperature below 0° C., it is desired to have been produced by heating the separated coprecipitates at a temperature approximately in the range of 200° C. to 500° C.

The ultra-fine gold particle-immobilized oxide of the present invention is further useful as a catalyst for reducing such nitrogen oxides as NO and $NO_2$ with hydrogen and carbon monoxide, for example.

Since the ultra-fine gold particle-immobilized oxide of this invention exhibits an extremely high catalytic activity for oxidation even at relatively low temperatures in the neighborhood of normal room temperature, it can be utilized as a sensor device for such inflammable gases as hydrogen, carbon monoxide, methanol, and hydrocarbons. The utilization as an inflammable gas sensor device is accomplished, for example, by coating a coiled platinum wire with sintered granules of ultra-fine gold particle-immobilized metal oxide or by superposing on a platelike thermistor a thick layer of ultra-fine gold particle-immobilized metal oxide. When the sensor device contacts the air containing an inflammable gas, the inflammable gas are oxidized on the sensor device surface and emits heat of combustion. The platinum wire coated with the sintered granules, therefore, can detect the presence of the inflammable gas in the air because the heat of combustion elevates the temperature of the platinum wire and proportionately increases the electric resistance thereof. The thermistor covered with the thick layer detects the elevation of the temperature of itself due to the heat of combustion.

In the case of the oxide immobilizing the ultra-fine gold is such a metal compound as tin oxide, zinc oxide, strontium titanate, or barium titanate which exhibits semiconductivity, the inflammable gas can be detected since the electric resistance of the oxide is varied by the surface adsorption, the reaction, etc. of the inflammable gas.

When a white metal oxide such as titanium oxide or alumina is used as the carrier, the ultra-fine gold particle-immobilized oxide, can be used as a pigment because it assumes a peculiar reddish purple, bluish purple, or blue color, depending on the diameter and shape of the ultra-fine gold particle, the dielectric constant of the carrier, and the like.

By the method of this invention, there can be obtained a metal oxide having strongly immobilized thereon ultra-fine gold particles uniform in diameter. Furthermore, this invention allows the ultra-fine gold particles to be immobilized on titanium oxide or tin oxide on which the conventional technique has been unable to deposit gold in the form of ultra-fine particles. This immobilization of the ultra-fine gold particle can be effected in a relatively short time and with high efficiency on compounds of varying forms.

The ultra-fine gold particle-immobilized metal oxide obtained by this invention is highly useful as oxidation catalyst, reduction catalyst, inflammable gas sensor device, etc. It can also be used as a pigment.

Now, this invention will be described below more specifically with reference to working examples.

EXAMPLE 1

To 200 ml of an aqueous solution having 22.3 g (0.21 mol) of sodium carbonate ($Na_2CO_3$) dissolved therein, 300 ml of an aqueous solution having 50 g (0.05 mol) of an aqueous 24 wt % titanium sulfate [$Ti(SO_4)_2$] solution and 1.08 g (0.0026 mol) of chloroauric acid ($HAuCl_4 \cdot 4H_2O$) dissolved therein was added dropwise over a period of 30 minutes. After 5 minutes following the completion of the dropwise addition, the resultant aqueous suspension of coprecipitate and 400 ml of an aqueous solution saturated with magnesium citrate [$Mg_3(C_6H_5O_7)_2$] (6.0 g/liter) (having citric acid concentration of $0.0026 \times 6$ mol) were continuously stirred for aging for 1 hour. At the end of this aging, the aqueous solution had a pH of 8.3. The coprecipitate consequently obtained was thoroughly washed with water, dried in a vacuum, and further fired in the air at 400° C. for 5 hours, to obtain a Au-immobilized $TiO_2$ j(atomic ratio of Au/Ti=1/19) catalyst. For comparison, a similar catalyst was obtained by following the procedure described above, except that the addition of magnesium citrate was omitted. This catalyst was tested for catalytic activity with respect to oxidation of carbon monoxide (CO) or hydrogen ($H_2$) by preparing a catalyst bed of 0.20 g of the portion of 70 to 120 mesh obtained by sieving the catalyst and passing the air containing 1% by volume of carbon monoxide or hydrogen at a flow rate of 67 ml/minute.

Figure 3:
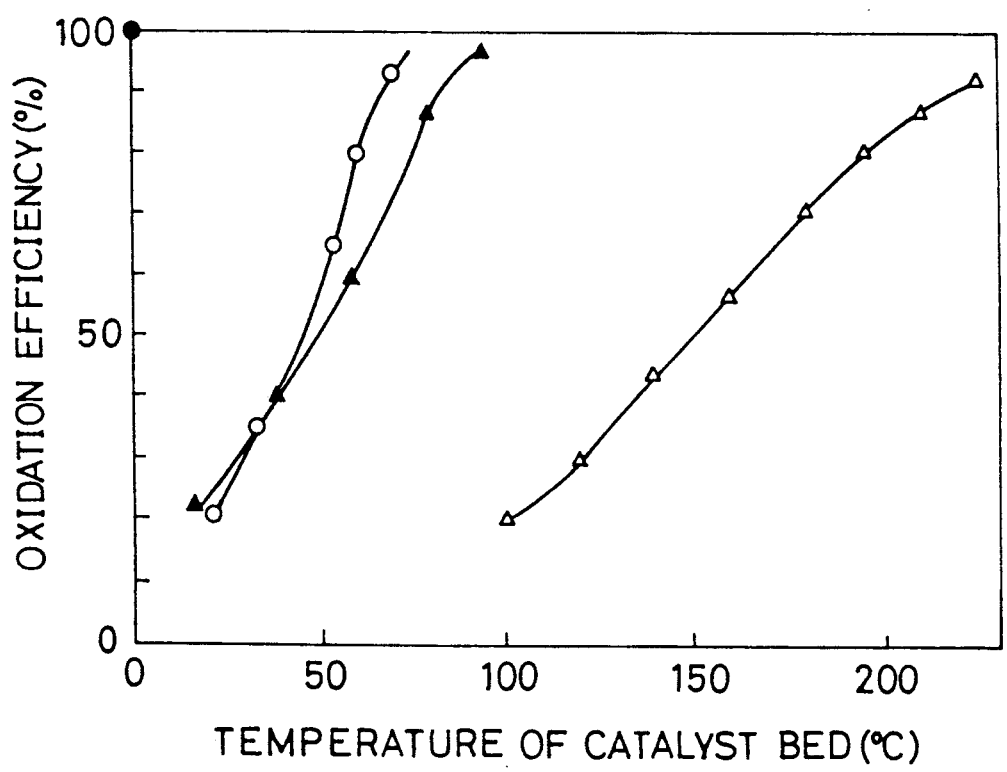
FIG. 3 is a diagram showing the relation between the temperature of catalyst bed and the conversion of oxidation determined as indicated in Example 1.

The relation between the temperature of the catalyst bed and the conversion of oxidation is shown in FIG. 3. In the Figure, the data of the oxidation of CO on the sample involving the addition of magnesium citrate are indicated by filled circles (●), those of the oxidation of $H_2$ on the sample involving the addition of magnesium citrate are indicated by empty circles (○), those of the oxidation of CO on the sample not involving the addition of magnesium citrate are indicated by filled triangles (●), and those of the oxidation of $H_2$ on the sample not involving the addition of magnesium citrate are indicated by empty triangles (Δ), respectively.

It is clearly noted from FIG. 3 that when the sample was made with the addition of magnesium citrate after the formation of the coprecipitate, the oxidation of carbon monoxide an that of hydrogen occurred at lower temperatures, indicating that the catalyst's activity in the oxidation was markedly improved.

EXAMPLE 2

Ultra-fine gold particle-immobilized metal oxides were prepared by the same procedure as in Example 1 except that the calcination temperature was varied to 110° C., 200° C., 300° C., 400° C., 500° C., 600° C., and 800° C. The resultant Au-immobilized $TiO_2$ catalyst were tested for catalytic activity in oxidation in the same manner as in Example 1.

Parameters for the catalytic activity for oxidation $T_{\frac{1}{2}}[CO]$ and $T_{\frac{1}{2}}[H_2]$ used hereinafter will be described.

The ultra-fine gold particle-immobilized oxide produced by the method of the present invention was used as a catalyst bed. CO or $H_2$ was allowed to flow through the catalyst bed under heating. The conversion in the oxidation of CO or $H_2$ varied depending on the temperature of the catalyst bed. The temperature where the conversion in the oxidation of CO passed through the catalyst bed was 50% was indicated by $T_{\frac{1}{2}}[CO]$. Similarly the temperature where the conversion in the oxidation of $H_2$ passed through the catalyst bed was 50% was indicated by $T_{\frac{1}{2}}[H_2]$.

In FIG. 3, for example, the curve connecting empty circles shows that when the temperature of the catalyst bed was 50° C., the conversion of $H_2$ passed through the catalyst bed reached 50%. Therefore, the catalytic activity for this curve is expressed by $T_{\frac{1}{2}}[H_2]=50°$ C. The curve connecting empty triangles shows that when the temperature of the catalyst bed was 150° C., the conversion of $H_2$ passed through the catalyst bed reached 50%. In this case, therefore, the catalytic activity for the curve is expressed by $T_{\frac{1}{2}}[H_2]=150°$ C. These indications mean that the lower the temperature of the catalyst bed is, the more rapid the low-temperature reaction, i.e. the higher the catalytic activity is.

Figure 4:
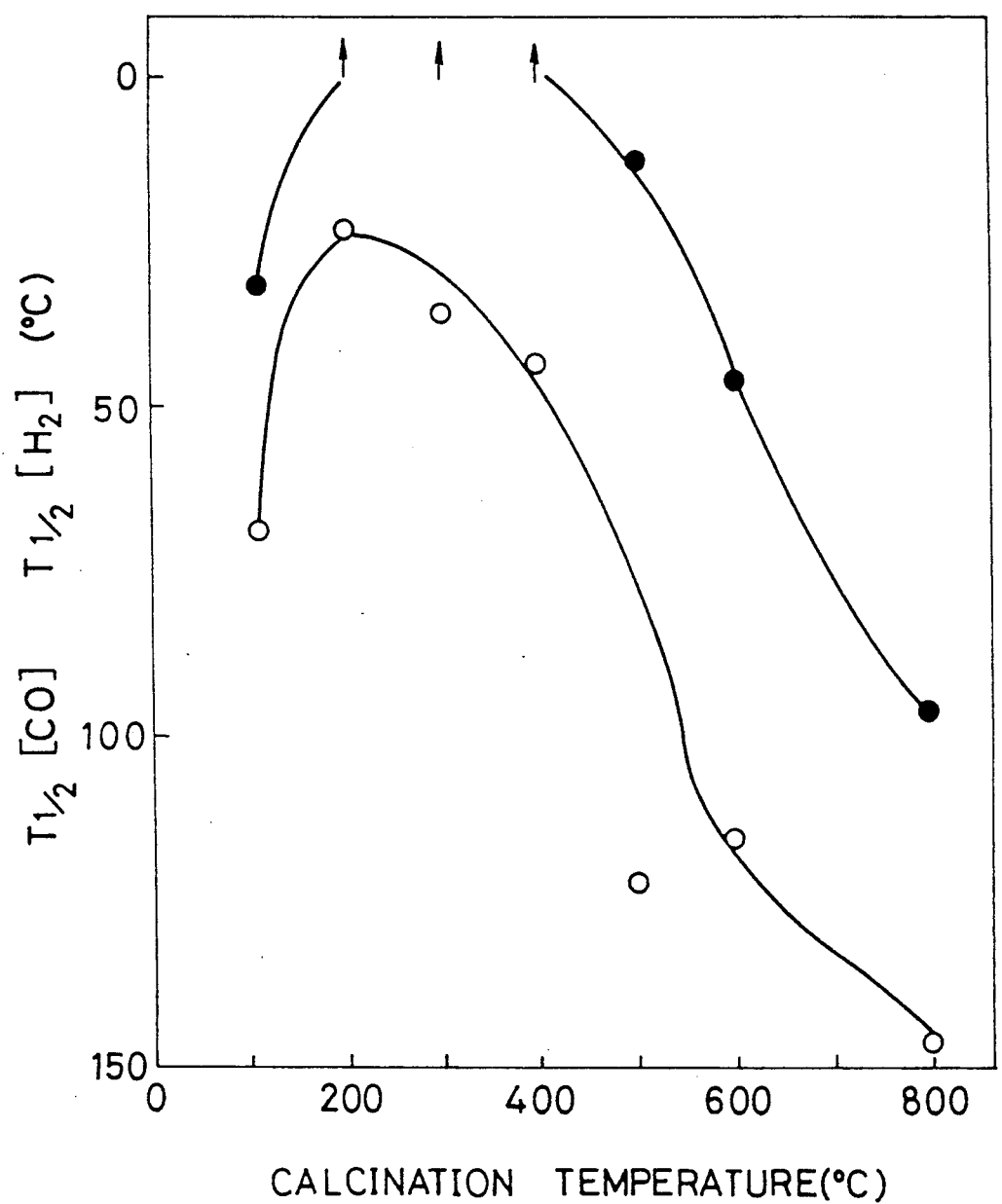
FIG. 4 is a diagram showing the relation between the calcination temperature and $T_{\frac{1}{2}}[CO$ and $T_{\frac{1}{2}}[H_2]$ during the course of production of a catalyst in Example 2.

FIG. 4 shows the relation between $T_{\frac{1}{2}}[CO]$ and $T_{\frac{1}{2}}[H_2]$ and the calcination temperature of the catalyst obtained by the Example 2. In the diagram, the curve of filled circles (●) represents the data with CO and that of empty circles (○) the data with $H_2$. In the case of the oxidation of CO, since the conversion was 100% even at 0° C., the pertinent portion of the curve is indicated with arrow marks (↑). The catalyst prepared by calcining at temperatures of 200° C. to 400° C. showed the highest degree of catalytic activity. Even those using lower calcination temperatures and those using higher calcination temperatures showed higher degrees of activity than the conventional gold catalyst.

EXAMPLE 3

To 500 ml of an aqueous solution having 22.3 g (0.21 mol) of sodium carbonate ($Na_2CO_3$) and 1.0 g (0.0033 mol as citric acid ion) of magnesium citrate [$Mg_3(C_6H_5O_7)_2$] dissolved therein and kept at 50° C., 300 ml of an aqueous solution having 50 g (0.05 mol) of an aqueous 24 wt % titanium sulfate [$Ti(SO_4)_2$] solution and 1.08 g (0.0026 mol) of chloroauric acid $HAuCl_4 \cdot 4H_2O$) dissolved therein and heated in advance to 50° C. was added dropwise over a period of 5 minutes. After completion of the dropwise addition, the resultant mixture was stirred continuously for aging at 50° C. for one hour. At the end of the aging, the pH of the solution was 8.4. The coprecipitate consequently obtained was thoroughly washed with water, dried overnight at 120° C., and then calcined in air at 400° C. for 5 hours, to obtain a Au-immobilized $TiO_2$ (atomic ratio of Au/Ti=1/19) catalyst.

When the catalyst was tested for activity by following the procedure of Example 1, the results were $T_{\frac{1}{2}}[CO]=19°$ C., and $T_{\frac{1}{2}}[H_2]=114°$ C.

EXAMPLE 4

To an aqueous solution having 22.3 g (0.21 mol) of sodium carbonate ($Na_2CO_3$), 22.3 g (0.21 mol) of magnesium citrate, and 7.0 g (0.024 mol as citric acid ion) of trisodium citrate ($C_6H_5O_7Na_3$) dissolved therein and kept at 0° C., 300 ml of an aqueous solution having 50 g (0.05 mol) of an aqueous 24 wt % titanium sulfate [$Ti(SO_4)_2$] solution and 1.08 g (0.0026 mol) of chloroauric acid $HAuCl_4 \cdot 4H_2O$) dissolved therein and heated in advance to 50° C. was added dropwise over a period of 5 minutes. After completion of the dropwise addition, the resultant mixture was stirred continuously for aging at 50° C. for one hour. At the end of the aging, the pH of the solution was 7.9. The coprecipitate consequently obtained was thoroughly washed with water, dried overnight at 120° C., and then calcined in air at 400° C. for 5 hours, to obtain a Au-immobilized $TiO_2$ (atomic ratio of Au/Ti=1/19) catalyst.

When this catalyst was tested for activity by following the procedure of Example 1, the conversion of CO oxidation reached 100% even at 0° C. and $T1/2[H_2]$ was 101° C.

EXAMPLE 5

To 2 liters of an aqueous solution having 145 g (1.05 mols) of potassium carbonate ($K_2CO_3$) dissolved therein and kept at 70° C., 3 liters of an aqueous solution having 250 g (0.25 mol) of an aqueous 24 wt % titanium sulfate [$Ti(SO_4)_2$] solution and 5.4 g (0.013 mol) of chloroauric acid ($HAuCl_4 \cdot 4H_2O$) dissolved therein was added dropwise. After 10 minutes following the completion of the dropwise addition, the resultant aqueous suspension of coprecipitate and 2 liters of an aqueous 0.04 M citric acid ($C_6H_8O_7$) solution were continuously stirred for aging at 70° C. for 2 hours. At the end of the aging, the pH of the solution was 7.5. The coprecipitate consequently obtained was thoroughly washed with water, dried in a vacuum, and then fired in air at 400° C. for 15 hours, to obtain a Au-immobilized $TiO_2$ (atomic ratio of Au/Ti=1/19) catalyst.

When this catalyst was tested for activity by following the procedure of Example 1, the conversion of CO oxidation reached 76% at 0° C. and $T_{\frac{1}{2}}[H_2]$ was 52° C.

EXAMPLE 6

To 200 ml of an aqueous solution having 11.1 g (0.1 mol) of sodium carbonate ($Na_2CO_3$) dissolved therein, 200 ml of an aqueous solution having 25 g (0.025 mol) of an aqueous 24 wt % titanium sulfate [$Ti(SO_4)_2$] solution and 0.54 g (0.0013 mol) of chloroauric acid ($HAuCl_4.4H_2O$) dissolved therein was added dropwise over a period of 10 minutes. After 10 minutes following the completion of this dropwise addition, the resultant aqueous suspension of coprecipitate and 200 ml of an aqueous 0.04 M potassium tartrate (KOOC.CHOH.CHOH.COOK) were continuously stirred for aging for 1 hour. At the end of the aging, the pH of the solution was 8.0. The coprecipitate consequently obtained was thoroughly washed with water, dried in a vacuum, and then calcined in air at 400° C. for 15 hours, to obtain a Au-immobilized $TiO_2$ (atomic ratio of Au/Ti=1/19) catalyst.

EXAMPLE 7

To 150 ml of an aqueous solution having 19.1 g (0.18 mol) of sodium carbonate dissolved therein, 200 ml of an aqueous solution having 16.1 g (0.025 mol) of an aqueous 24 wt % titanium trichloride ($TiCl_3$) solution, 8.3 ml of 12 N hydrochloric acid, 30 ml of aqueous hydrogen peroxide solution, and 0.54 g (0.0013 mol) of chloroauric acid ($HAuCl_4.4H_2O$) dissolved therein was added dropwise over a period of 15 minutes. After 15 minutes following the completion of this dropwise addition, the resultant aqueous suspension of coprecipitate and 200 ml of an aqueous 0.04 M maleic acid (HOOC.CH.CH.COOH) solution were continuously stirred for aging for 2 hours. At the end of the aging, the pH of the solution was 7.3. The coprecipitate consequently obtained was thoroughly washed with water, dried in a vacuum, and then calcined in air at 400° C. for 15 hours, to obtain a Au-immobilized $TiO_2$ (atomic ratio of Au/Ti=1/19) catalyst.

EXAMPLE 8

To 150 ml of an aqueous solution having 19.1 g (0.18 mol) of sodium carbonate, 200 ml of an aqueous solution having 16.1 g (0.025 mol) of an aqueous 24 wt % titanium trichloride ($TiCl_3$) solution, 8.3 ml of 12 N hydrochloric acid, 30 ml of aqueous hydrogen peroxide solution, and 0.54 g (0.0013 mol) of chloroauric acid ($HAuCl_4.4H_2O$) dissolved therein was added dropwise over a period of 15 minutes. After 15 minutes following the completion of this dropwise addition, the resultant aqueous suspension of coprecipitate and 400 ml of an aqueous 0.02 M barium succinate solution were continuously stirred for aging for 2 hours. At the end of the aging, the pH of the solution was 8.2. The coprecipitate consequently obtained was thoroughly washed with water, dried in a vacuum, and then calcined in air at 400° C. for 15 hours, to obtain a Au-immobilized $TiO_2$ (atomic ratio of Au/Ti=1/19) catalyst.

EXAMPLE 9

To 150 ml of an aqueous solution having 19.1 g (0.18 mol) of sodium carbonate dissolved therein, 200 ml of an aqueous solution having 16.1 g (0.025 mol) of an aqueous 24 wt % titanium trichloride ($TiCl_3$) solution, 8.3 ml of 12 N hydrochloric acid, 30 ml of an aqueous hydrogen peroxide solution, and 0.54 g (0.0013 mol) of chloroauric acid $HAuCl_4.4H_2O$) dissolved therein was added dropwise over a period of 15 minutes. After 15 minutes following the completion of this dropwise addition, the resultant aqueous suspension of coprecipitate and 400 ml of an aqueous 0.02 M manganese oxalate solution were continuously stirred for aging for 2 hours. At the end of the aging, the pH of the solution was 7.9. The coprecipitate consequently obtained was thoroughly washed with water, dried in a vacuum, and then calcined in air at 400° C. for 15 hours, to obtain a Au-immobilized $TiO_2$ (atomic ratio of Au/Ti=1/19) catalyst.

EXAMPLE 10

To 150 ml of an aqueous solution having 19.1 g (0.18 mol) of sodium carbonate dissolved therein, 200 ml of an aqueous solution having 16.1 g (0.025 mol) of an aqueous 24 wt % titanium trichloride ($TiCl_3$) solution, 8.3 ml of 12 N hydrochloric acid, 30 ml of an aqueous hydrogen peroxide solution, and 0.54 g (0.0013 mol) of chloroauric acid $HAuCl_4.4H_2O$) dissolved therein was added dropwise over a period of 15 minutes. After 15 minutes following the completion of this dropwise addition, the resultant aqueous suspension of coprecipitate and 400 ml of an aqueous 0.02 M cobalt malonate solution were continuously stirred for aging for 2 hours. At the end of the aging, the pH of the solution was 7.8. The coprecipitate consequently obtained was thoroughly washed with water, dried in a vacuum, and then calcined in air at 400° C. for 15 hours, to obtain a Au-immobilized $TiO_2$ (atomic ratio of Au/Ti=1/19) catalyst.

EXAMPLE 11

To 200 ml of an aqueous solution having 11.1 g (0.1 mol) of sodium carbonate ($Na_2CO_3$) dissolved therein, 200 ml of an aqueous solution having 25 g (0.025 mol) of an aqueous 24 wt % titanium sulfate [$Ti(SO_4)_2$] solution and 0.54 g (0.0013 mol) of chloroauric acid $HAuCl_4.4H_2O$) dissolved therein was added dropwise over a period of 10 minutes. After 10 minutes following the completion of this dropwise addition, the resultant aqueous suspension of coprecipitate and 400 ml of an aqueous 0.02 M nickel glutarate solution were continuously stirred for aging for 1 hour. At the end of the aging, the coprecipitate consequently obtained was thoroughly washed with water, dried in a vacuum, and then calcined in air at 400° C. for 15 hours, to obtain a Au-immobilized $TiO_2$ (atomic ratio of Au/Ti=1/19) catalyst.

EXAMPLE 12

To 200 ml of an aqueous solution having 11.1 g (0.1 mol) of sodium carbonate ($Na_2CO_3$) dissolved therein, 200 ml of an aqueous solution having 25 g (0.025 mol) of an aqueous 24 wt % titanium sulfate [$Ti(SO_4)_2$] solution and 0.54 g (0.0013 mol) of chloroauric acid $HAuCl_4.4H_2O$) dissolved therein was added dropwise over a period of 10 minutes. After 10 minutes following the completion of this dropwise addition, the resultant aqueous suspension of coprecipitate and 400 ml of an aqueous 0.02 M strontium malate were continuously stirred for aging for 1 hour. At the end of the aging, the pH of the solution was 8.2. The coprecipitate consequently obtained was thoroughly washed with water, dried under a vacuum, and then calcined in air at 400° C. for 15 hours, to obtain a Au-immobilized $TiO_2$ (atomic ratio of Au/Ti=1/19) catalyst.

EXAMPLE 13

To 200 ml of an aqueous solution having 11.1 g (b 0.1 mol) of sodium carbonate ($Na_2CO_3$) dissolved therein, 200 ml of an aqueous solution having 25 g (0.025 mol) of an aqueous 24 wt % titanium sulfate [$Ti(SO_4)_2$] solution and 0.54 g (0.0013 mol) of chloroauric acid $HAuCl_4 \cdot 4H_2O$) dissolved therein was added dropwise over a period of 10 minutes. After 10 minutes following the completion of this dropwise addition, the resultant aqueous suspension of coprecipitate and 200 ml of an aqueous 0.04 M calcium glycolate solution were continuously stirred for aging for 1 hour. At the end of this aging, the pH of the solution was 8.1. The coprecipitate consequently obtained was thoroughly washed with water, dried under a vacuum, and then calcined in air at 400° C. for 15 hours, to obtain a Au-immobilized $TiO_2$ (atomic ratio of Au/Ti=1/19) catalyst.

EXAMPLE 14

The catalyst obtained in Examples 6 to 13 were tested for catalytic activity for oxidation by following the procedure of Example 1. The results were as shown in Table 1. For comparison, a catalyst was prepared by the coprecipitation method without the addition of a carboxylic acid compound and this catalyst was similarly tested. The results are also shown.

TABLE 1

| Catalyst | $T_{\frac{1}{2}}$ [CO] (°C.) | $T_{\frac{1}{2}}$ [$H_2$] (°C.) |
| --- | --- | --- |
| Example 6 | <0 | 45 |
| Example 7 | <0 | 53 |
| Example 8 | <0 | 51 |
| Example 9 | 5 | 68 |
| Example 10 | <0 | 56 |
| Example 11 | <0 | 49 |
| Example 12 | <0 | 59 |
| Example 13 | 13 | 76 |
| Without addition of carboxylic acid compound | 48 | 149 |

EXAMPLE 15

To 500 ml of an aqueous solution having 11.1 g (0.1 mol) of sodium carbonate ($Na_2CO_3$) dissolved therein, 500 ml of an aqueous solution having 25 g (0.025 mol) of an aqueous 24 wt % titanium sulfate [$Ti(SO_4)_2$] solution and 0.54 g (0.0013 mol) of chloroauric acid $HAuCl_4 \cdot 4H_2O$) dissolved therein was added dropwise over a period of 10 minutes. After 10 minutes following the dropwise addition, the resultant aqueous suspension of coprecipitate and a varying amount in the range of 33 to 1,000 ml of an aqueous 0.04 M calcium oxalate solution were continuously stirred for aging for 1 hour. The coprecipitate consequently obtained was thoroughly washed with water, dried under a vacuum, and then calcined in air at 400° C. for 15 hours, to obtain a Au-immobilized $TiO_2$ (atomic ratio of Au/Ti=1/19) catalyst.

Figure 5:
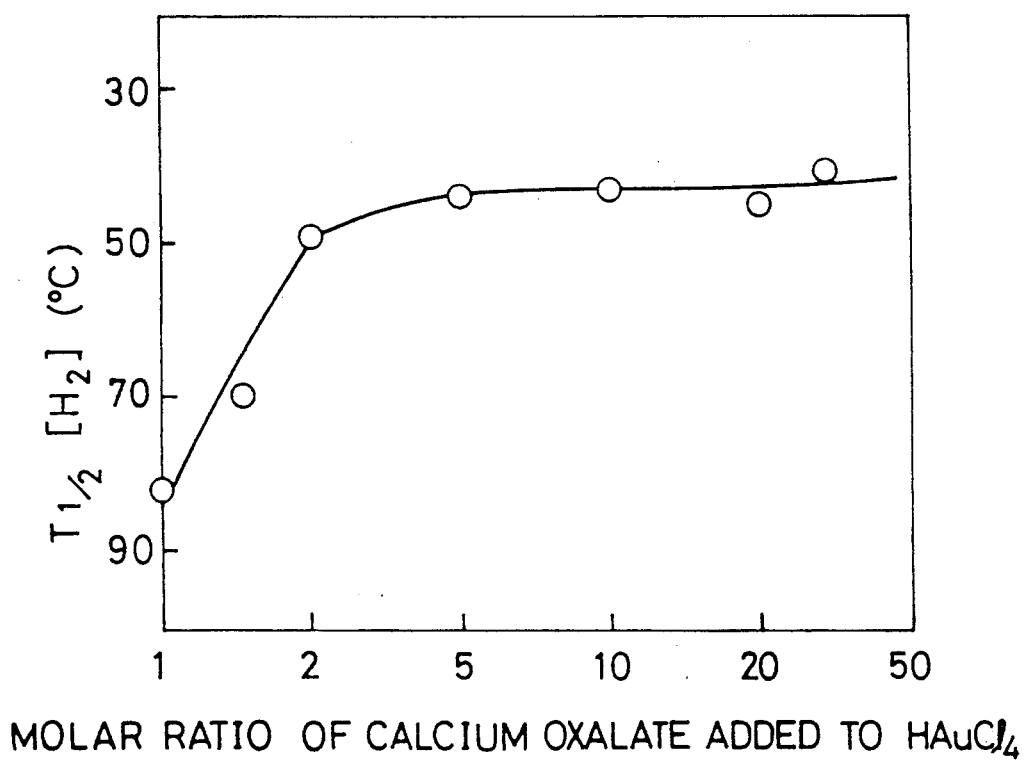
FIG. 5 is a diagram showing the relation between the amount of calcium oxalate used as a carboxylate and $T_{\frac{1}{2}}[H_2]$ indicated in Example 15.

The catalysts using calcium oxalate in varying amounts were tested for catalytic activity for oxidation by following the procedure of Example 1. The results were as shown in FIG. 5 and indicate that the amount of calcium oxalate to be added is required to exceed 1 mol and desired to exceed 2 mols per mol of gold. This amount of calcium oxalate has no upper limit in particular. Since this compound has a small dissociation constant, the amount of its addition may exceed even 30 mols per mol of gold.

EXAMPLE 16

To 200 ml of an aqueous solution having 11.1 g (0.1 mol) of sodium carbonate ($Na_2CO_3$) dissolved therein, 200 ml of an aqueous solution having 25 g (0.025 mol) of an aqueous 24 wt % titanium sulfate [$Ti(SO_4)_2$] solution and 0.54 g (0.0013 mol) of chloroauric acid $HAuCl_4 \cdot 4H_2O$) dissolved therein was added dropwise over a period of 10 minutes. After 10 minutes following the completion of this dropwise addition, the resultant aqueous suspension of coprecipitate and 400 ml of an aqueous 0.02 M magnesium citrate [$Mg_3(C_6H_5O_7)_2$] solution and a varying amount of an aqueous 1 M sodium carbonate solution selected to give a varying pH value to the resultant suspension were continuously stirred for aging for 1 hour. Where the pH value of the suspension was selected below 7, citric acid was used in stead of magnesium citrate. The coprecipitate consequently obtained was thoroughly washed with water, dried under a vacuum, and then calcined in air at 400° C. for 15 hours, to obtain a Au-immobilized $TiO_2$ (atomic ratio of Au/Ti=1/19) catalyst.

Figure 6:
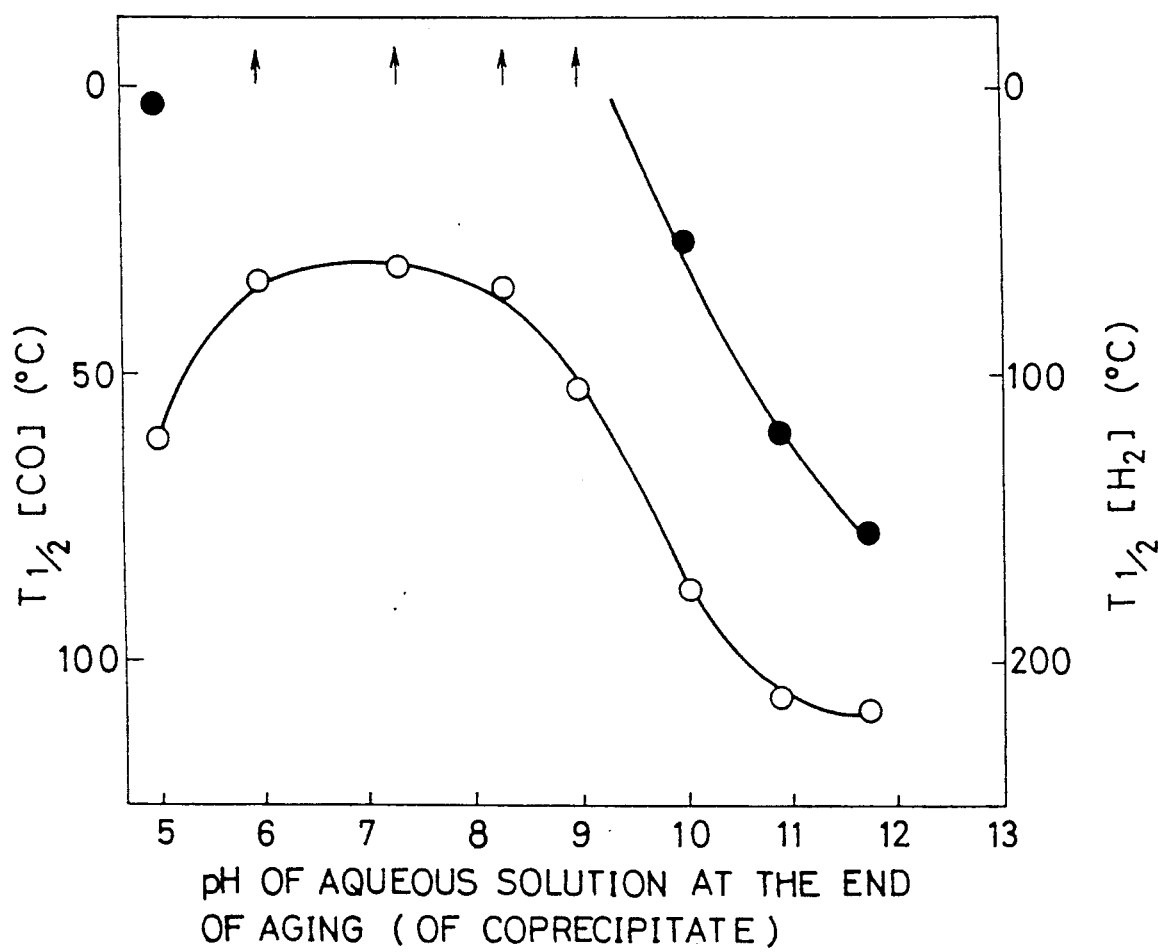
FIG. 6 is a diagram showing the relation between the pH of the aqueous solution and $T_{\frac{1}{2}}[CO]$ and $T_{\frac{1}{2}}[H_2]$ at the end of the aging of the coprecipitate as indicated in Example 16.

The catalysts prepared by using varying pH values for aging were tested for catalytic activity by following the procedure of Example 1. The results were as shown in FIG. 6. In the Figure, the curve of filled circles (●) represent data of $T_{\frac{1}{2}}$[CO] and the curve of empty circles (○) represent data of $T_{\frac{1}{2}}$[$H_2$]. From these results, it is clearly noted that the pH value for aging is required to be in the range of 5 to 12 and desired to be in the range of 6 to 8.

EXAMPLE 17

To an aqueous solution having 22.3 g (0.21 mol) of sodium carbonate ($Na_2CO_3$) and such an amount of magnesium citrate [$Mg_3(C_6H_5O_7)_2$] as to contain 6 mols of citric acid ion per mol of gold dissolved therein and kept at 50° C., 300 ml of an aqueous solution having 50 g (0.05 mol) of an aqueous 24 wt % titanium sulfate [$Ti(SO_4)_2$] solution and a varying amount of chloroauric acid ($HAuCl_4 \cdot 4H_2O$) dissolved therein was added dropwise over a period of 5 minutes. After the dropwise addition was completed, the resultant mixed solution was continuously stirred for aging at 50° C. for 1 hour. At the end of the aging, the pH of the solution was in the range of 8.0 to 8.4. The coprecipitate consequently obtained was thoroughly washed with water, dried overnight at 120° C., and then calcined in air at 400° C. for 5 hours, to obtain a $TiO_2$ catalyst having Au-immobilized in a varying amount (atomic ratio of Au/Ti=1/333 to 1/9) catalyst.

Figure 7:
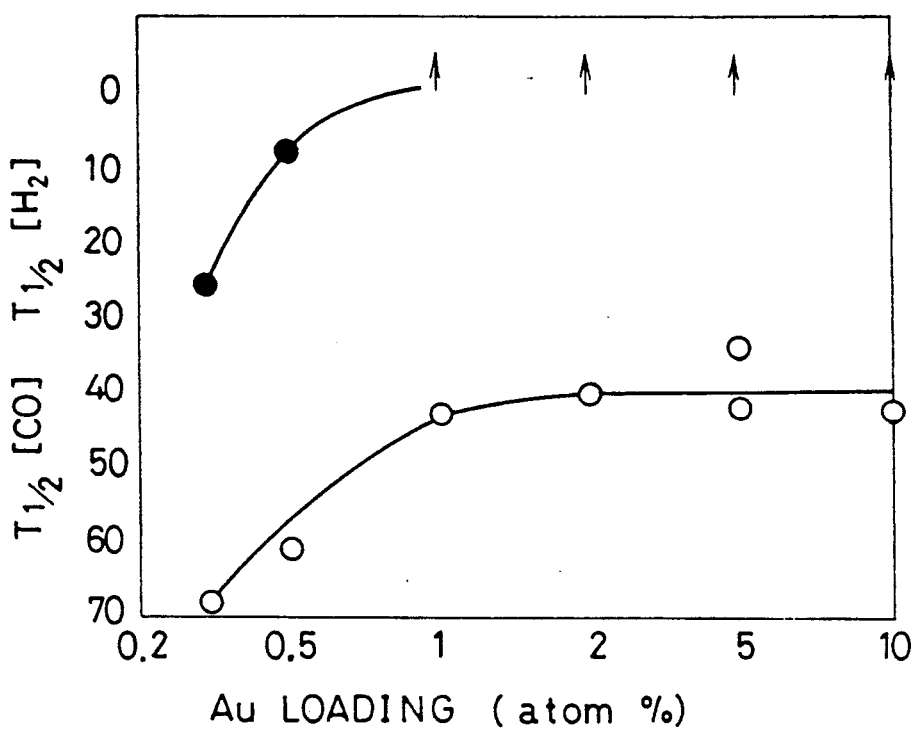
FIG. 7 is a diagram showing the relation between the amount of gold immobilized on a catalyst and $T_{\frac{1}{2}}[CO]$ and $T_{\frac{1}{2}}[H_2]$ as indicated in Example 17.

The catalysts obtained as described above were tested for catalytic activity by following the procedure of Example 1. The results were as shown in FIG. 7. It is clearly noted from the results that the amount of gold to be immobilized is desired to exceed 0.3 atom % [(Au/Au + carrier metal)×100], preferably 1 atom %. In the diagram, the curve of filled circles (●) represent data of $T_{\frac{1}{2}}[CO]$ and the curve of empty circles (○) represent data of $T_{\frac{1}{2}}[H_2]$.

EXAMPLE 18

The two gold-immobilized titania catalysts prepared by the procedure of Example 1 were subjected to X-ray diffraction analysis to determine the effect of addition of magnesium citrate.

FIG. 1 is a powder X-ray diffraction diagram obtained for a sample involving the addition of magnesium citrate and FIG. 2 is a powder X-ray diffraction diagram obtained for a sample without involving the addition of magnesium citrate.

It is noted from FIG. 1 that the sample prepared by a procedure involving the addition of magnesium citrate after the coprecipitation showed absolutely no diffraction peak corresponding to metallic gold, suggesting that the gold particles were very small. From the powder X-ray diffraction pattern shown in FIG. 2, it is noted that the sample prepared by the conventional coprecipitation method involving no addition of magnesium citrate showed a diffraction peak corresponding to metallic gold. The particle diameter of gold estimated from the half-value width of the diffraction peak of the gold (111) plane was about 5 nm.

When the sample prepared by the procedure involving the addition of magnesium citrate after the coprecipitation was observed under a high-resolution transmission type electron microscope, gold was found to be immobilized in the form of very small particles measuring about 1 to 2 nm in diameter or in the form of clusters of a smaller diameter on titanium oxide.

EXAMPLE 19

To 300 ml of an aqueous solution having 12.4 g of an solution of tin tetrachloride ($SnCl_4$) possessing a specific gravity of 2.28 and 0.400 g of chloroauric acid ($HAuCl_4.4H_2O$) dissolved therein, 300 ml of an aqueous solution having 15.5 g of sodium carbonate ($Na_2CO_3$) dissolved therein was added over a period of 1 minute and, after an interval of 20 minutes thereafter, 150 ml of an aqueous 0.02 M magnesium citrate solution was added. The resultant mixed solution was stirred for 1 hour. At the end of the aging, the pH of the solution was 8.5. The coprecipitate consequently obtained was thoroughly washed with water, dried overnight at 120° C., and then calcined in air at 400° C. for 10 hours, to obtain a $Au/SnO_2$ (atomic ratio of Au/Sn =1/49) catalyst.

This catalyst was tested for activity by following the procedure of Example 1. The results were $T_{\frac{1}{2}}[CO]=68°$ C. and $T_{\frac{1}{2}}[H_2]=110°$ C. In the case of a sample prepared by following the procedure described above, except that the addition of magnesium citrate was omitted, the results of the same test were $T_{\frac{1}{2}}[CO]=123°$ C. and $T_{\frac{1}{2}}[H_2]=145°$ C., indicating that the addition of magnesium citrate notably improved catalytic activity.

When the sample resulting from calcination at 400° C. was fired in air at 800° C. for 5 hours, the results of the same test were $T_{\frac{1}{2}}[CO]=268°$ C. and $T_{\frac{1}{2}}[H_2=316°$ C., indicating appreciably reduced catalytic activity. However, the product had a clear light bluish purple tone suitable for a pigment.

EXAMPLE 20

To an aqueous solution of 14.9 g of sodium carbonate ($Na_2CO_3$) and 0.5 g of magnesium citrate, 500 ml of an aqueous solution having 12.4 g of an aqueous solution of tin tetrachloride ($SnCl_4$) possessing a specific gravity of 2.28, 0.184 g of antimony penetachloride ($SbCl_5$), and 0.206 g of chloroauric acid ($HAuCl_4.4H_2O$)) dissolved therein was added dropwise over a period of 10 minutes. The resultant mixed solution was left aging for 1 hour. At the end of aging, the pH of the solution was 8.4. The coprecipitate consequently obtained was thoroughly washed with water, dried overnight at 120° C., and then calcined in air at 400° C. for 5 hours, to obtain a $Au/Sb^{5+}$ dope $SnO_2$ (atomic ratio of Au:Sb:Sn =1:1:99) oxide semiconductor catalyst.

When this catalyst was tested for catalytic activity by following the procedure of Example 1, the results were $T_{\frac{1}{2}}[CO]=101°$ C. and $T_{\frac{1}{2}}[H_2]=124°$ C.

EXAMPLE 21

To 100 ml of an aqueous solution having 5.0 g of sodium carbonate ($Na_2CO_3$) dissolved therein and kept at 90° C., 250 ml of an aqueous solution having zinc nitrate [$Zn(NO_3)_2.6H_2O$] and 0.253 g of chloroauric acid ($HAuCl_4.4H_2O$) dissolved therein and heated in advance to 90° C. was added dropwise over a period of 30 minutes and, after an interval of 15 minutes thereafter, 100 ml of an aqueous 0.02 M barium tartrate solution was added. Even thereafter, the resultant mixed aqueous solution was kept heated at 90° C. and stirred for aging for one hour. At the end of the aging, the pH of the solution was 8.7. The coprecipitate consequently obtained was thoroughly washed with water, dried overnight under a vacuum, and then calcined in air at 400° C. for 16 hours, to obtain a Au/ZnO (atomic ratio of Au/Zn=1/49) catalyst.

When this catalyst was tested for activity by following the procedure of Example 1, the results were $T_{\frac{1}{2}}[CO]=85°$ C. and $T_{\frac{1}{2}}[H_2]=177°$ C.

EXAMPLE 22

To 100 ml of an aqueous solution having 4.7 g of aluminum nitrate [$Al(NO_3)_3.9H_2O$] and 0.273 g of chloroauric acid ($HAuCl_4.4H_2O$) dissolved therein, 100 ml of an aqueous solution having 1.0 g of sodium hydroxide dissolved therein was added dropwise over a period of 5 minutes and 100 ml of an aqueous 0.02 M cobalt citrate solution was subsequently added. The resultant mixed aqueous solution was stirred for aging for 2 hours. At the end of the aging, the pH of the solution was 8.2. The coprecipitate consequently obtained was thoroughly washed with water, dried overnight at 120° C., and then calcined in air at 400° C. for 14 hours, to obtain a $Au/Al_2O_3$ (atomic ratio of Au/Al=1/19) catalyst.

When this catalyst was tested for activity by following the procedure of Example 1, the results were $T_{\frac{1}{2}}[CO]=95°$ C. and $T_{\frac{1}{2}}[H_2]=105°$ C.

EXAMPLE 23

A gas-sensitive material for an inflammable gas sensor was produced by the following procedure.

A sintered film was made from the $Au/Sb^{5+}$ doped $SnO_2$ semiconductor obtained in Example 20 and two electrodes were connected thereto to measure electric resistance. Specifically, on the surface of an alumina substrate 10 mm×10 mm in size and 0.5 mm in thickness, two metallic electrodes (0.05 mm in width) were parallelly deposited with an interval of 1.0 mm. On the electrodes, a paste prepared from 5 mg of the $Au/Sb^{5+}$ doped $SnO_2$ particle and about 0.01 ml of water added thereto were applied. The resultant composite was dried at 120° C. for 12 hours and then fired in the air at 650° C. for 1 hour, to obtain a sintered film covering the electrodes. This sintered film was used as an inflammable gas sensor device. The device was tested to obtain the relation between device temperature and sensitivity.

The sensitivity for the detection of inflammable gas was expressed by the ratio of the magnitude of electric resistance of the gas sensor device in fresh air (Rair) to the magnitude of electric resistance of the element in the gas under test (Rgas).

Figure 8:
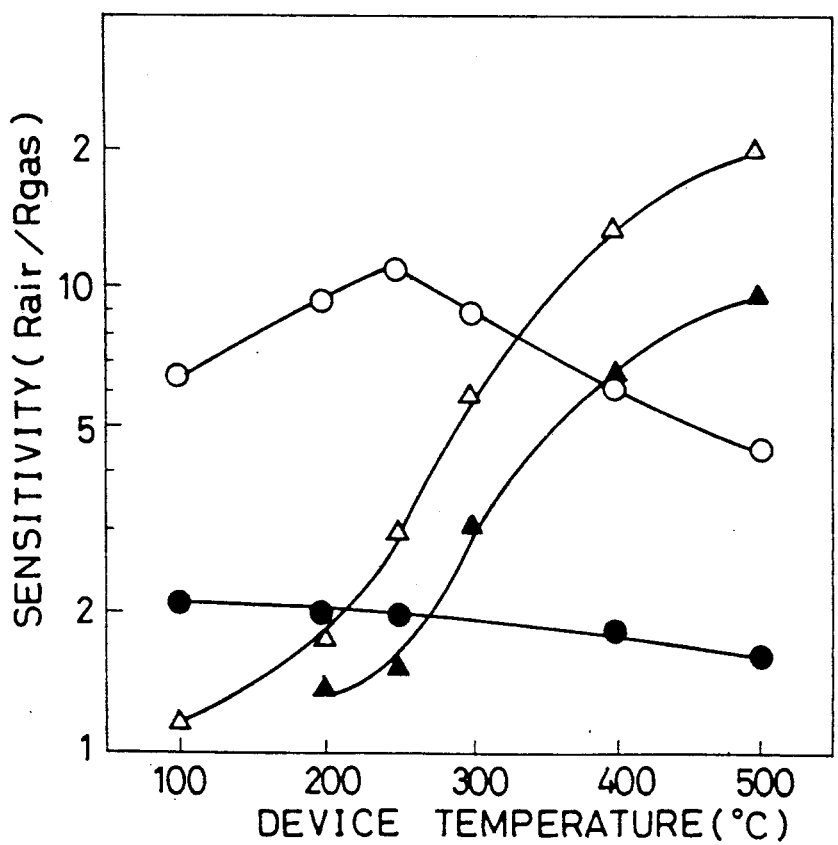
FIG. 8 is a diagram showing the relation between the temperature of the sensor device and the sensitivity of the obtained when an ultra-fine gold particle-immobilized oxide produced by the method of this invention is used as a gas sensor device.

The gas used for this test was air containing hydrogen or carbon monoxide. The results were as shown in FIG. 8. In FIG. 8, the curves of empty circles (○) and filled circles (●) represent the data obtained for air containing 300 ppm and 10 ppm of carbon monoxide, respectively and the curves of empty triangles (△) and filled triangles (▲) represent the data obtained for air containing 300 ppm and 100 ppm of hydrogen, respectively.

From the obtained results, it is clearly noted that the gas sensor device was capable of detecting the inflammable gas over a wide range of temperatures from 100° C. to 500° C. Since stable immobilization of gold in the form of ultra-fine particles was realized, the sensor device showed appreciably high sensitivity for carbon monoxide. These test results clearly indicate that the method of this invention is a highly effective way of preparing a gas-sensitive material for selective sensors to inflammable gases, particularly carbon monoxide.

EXAMPLE 24

The coprecipitates obtained in Example 4, Example 5, Example 15, Example 17, Example 19, and Example 22 were fired in air at varying temperatures. Consequently, the fired coprecipitates showed purplish colors peculiar to ultra-fine gold particles. The results were as shown in Table 2.

TABLE 2

| Example | Atomic ratio of Au/metal | Firing temperature | Tone |
| --- | --- | --- | --- |
| 4 | Au/Ti = 1/19 | 400° C. | Dark bluish purple |
| 5 | Au/Ti = 1/19 | 400° C. | Dark reddish purple |
| 15 | Au/Ti = 1/19 | 400° C. | Dark blue |
| 17 | Au/Ti = 1/199 | 400° C. | Light bluish purple |
| 19 | Au/Sn = 1/49 | 400° C. | Bluish gray |
| 19 | Au/Sn = 1/49 | 800° C. | Clear light bluish purple |
| 22 | Au/Al = 1/19 | 400° C. | Brownish beige |

From the test results, it is noted that the high-dispersion gold-immobilized catalyst prepared by the method of this invention is also useful as pigments for cosmetic articles, points, and glazes.

What is claimed is:

1. A method for the production of an ultra-fine gold particle-immobilized oxide, which method essentially consists of neutralizing an aqueous solution containing as substantially main components thereof a gold compound and a water-soluble metal salt by the addition of an alkali compound thereby giving rise to a coprecipitate, then adding to the resultant coprecipitate-containing aqueous solution at least one carboxylic acid compound selected from the group consisting of carboxylic acids and salts of said carboxylic acids and separating said coprecipitate from said aqueous solution, and heating the separated coprecipitate.

2. A method according to claim 1, wherein the concentration of said gold compound in said aqueous solution is in the range of $1 \times 10^{-2}$ mol/liter to $1 \times 10^{-5}$ mol/liter and the concentration of said water-soluble metal salt is in the range of 1 mol/liter to 0.01 mol/liter.

3. A method according to claim 1, wherein said carboxylic acid compound is added in such an amount that the concentration of carboxylic acid ion produced in consequence of dissociation of said compound in said coprecipitate-containing aqueous solution is in the range of 0.0001 mol/liter to 0.01 mol/liter.

4. A method according to claim 1, wherein said coprecipitate is allowed to age to such an extent after addition of said carboxylic acid compound that the pH of said aqueous solution is in the range of 5 to 12.

5. A method according to claim 1, wherein said gold compound is one member selected from the group consisting of chloroauric acid (HAuCl$_4$), sodium chloroaurate (NaAuCl$_4$), gold cyanide (AuCN), potassium gold cyanide trichloride {K[Au(CN)$_2$]}, and diethylamineauric acid trichloride [(C$_2$H$_5$)$_2$NH.AuCl$_3$].

6. A method according to claim 5, wherein said gold compound is chloroauric acid (HAuCl$_4$).

7. A method according to claim 1, wherein said water-soluble metal salt is at least one member selected from the group consisting of nitrates, sulfates, and chlorides of Cu, Fe, Co, Ni, Mn, Al, Ti, Zn, Sn, and Sb.

8. A method according to claim 7, wherein said water-soluble metal salt is at least one member selected from the group consisting of Ti(SO$_4$)$_2$, TiCl$_3$, SnCl$_4$, SbCl$_5$, Zn(NO$_3$)$_2$.6H$_2$O, and Al(NO$_3$)$_3$.9H$_2$O.

9. A method according to claim 1, wherein said carboxylic acid compound is at least one member selected from the group consisting of glutaric acid (HOOCCH$_2$CH$_2$CH$_2$COOH), glycolic acid (CH$_2$OH.COOH), oxalic acid (HOOC.COOH), lactic acid [CH$_3$.CH(OH).COOH], malonic acid (HOOC.CH$_2$.COOH), maleic acid (HOOC.CH=CH.COOH), succinic acid (HOOC.CH$_2$CH$_2$COOH), malic acid [HOOC.CH(OH).CH$_2$.COOH], tartaric acid [HOOC.CH(OH).CH(OH).COOH], citric acid [HOOC.CH$_2$.C(OH)(COOH).CH$_2$COOH], and potassium, sodium, magnesium, strontium, barium, manganese, cobalt, and nickel salts of said acids.

10. A method according to claim 9, wherein said carboxylic acid compound is one member selected from the group consisting of citric acid, maleic acid, magnesium citrate, trisodium citrate, potassium tartrate, barium succinate, manganese oxalate, calcium oxalate, cobalt malonate, nickel glutarate, strontium malate, calcium glycolate, barium tartrate, and cobalt citrate.

11. A method for the production of an ultra-fine gold particle-immobilized oxide, which method essentially consists of neutralizing an aqueous solution containing as substantial main components a gold compound, a water-soluble metal salt, and at least one carboxylic acid compound selected from the group consisting of carboxylic acids and salts of said carboxylic acids by the addition of an alkali compound thereby giving rise to a coprecipitate, separating said coprecipitate from said aqueous solution, and calcining the separated coprecipitate.

12. A method according to claim 11, wherein the concentration of said gold compound in said aqueous solution is in the range of $1 \times 10^{-2}$ mol/liter to $1 \times 10^{-5}$ mol/liter and the concentration of said water-soluble metal salt is in the range of 1 mol/liter to 0.01 mol/liter.

13. A method according to claim 11, wherein the amount of said carboxylic acid compound in said aqueous solution is such that the concentration of carboxylic acid ion produced in consequence of dissociation of said compound is in the range of 0.0001 mol/liter to 0.01 mol/liter.

14. A method according to claim 11, wherein said coprecipitate is allowed to age to such an extent that the pH of said aqueous solution is in the range of 5 to 12.

15. A method according to claim 11, wherein said gold compound is one member selected from the group consisting of chloroauric acid (HAuCl$_4$), sodium chloroaurate (NaAuCl$_4$), gold cyanide (AuCN), potassium {K[Au(CN)$_2$]}, and dictrylamineauric acid trichloride [(C$_2$H$_5$)$_2$NH.AuCl$_3$].

16. A method according to claim 15, wherein said gold compound is chloroauric acid (HAuCl$_4$).

17. A method according to claim 11, wherein said water-soluble metal salt is at least one member selected from the group consisting of nitrates, sulfates, and chlorides severally of Cu, Fe, Co, Ni, Mn, Al, Ti, Zn, Sn, and Sb.

18. A method according to claim 17, wherein said water-soluble metal salt is at least one member selected from the group consisting of Ti(SO$_4$)$_2$, TiCl$_3$, SnCl$_4$, SbCl$_5$, Zn(NO$_3$)$_2$.6H$_2$O, and Al(NO$_3$)$_3$.9H$_2$O.

19. A method according to claim 11, wherein said carboxylic acid compound is at least one member selected from the group consisting of glutaric acid (HOOCCH$_2$CH$_2$CHOOH), glycolic acid (CH$_2$O-HOOH), oxalic acid (HOOC.COOH), lactic acid [CH$_3$.CH(OH).COOH], malomic acid (HOOC.CH$_2$COOH), maleic acid (HOOC.CH=CH.COOH), succinic acid (HOOC.CH$_2$.CH$_2$COOH), malic acid [HOOC.CH(OH).CH$_2$.COOH], tartaric acid [HOOC.CH(OH).CH(OH).COOH], citric acid [HOOC.CH$_2$.C(OH)(COOH).CH$_2$COOH], and potassium, sodium, magnesium, strontium, barium, manganese, cobalt, and nickel salts of said acids.

20. A method according to claim 19, wherein said carboxylic acid compound is one member selected from the group consisting of citric acid, maleic acid, magnesium citrate, trisodium citrate, potassium tartrate, barium succinate, manganese oxalate, calcium oxalate, cobalt malonate, nickel glutarate, strontium malate, calcium glycolate, barium tartrate, and cobalt citrate.

* * * * *